United States Patent [19]
Cecchi

[11] Patent Number: 5,848,978
[45] Date of Patent: Dec. 15, 1998

[54] SURGICAL BIOPSY DEVICE

[75] Inventor: Michael Cecchi, Madison, Conn.

[73] Assignee: GenX International, Inc., Madison, Conn.

[21] Appl. No.: 557,524

[22] Filed: Nov. 14, 1995

[51] Int. Cl.⁶ .................................................. A61B 10/00
[52] U.S. Cl. .......................................................... 600/567
[58] Field of Search .................................. 600/564–567; 606/167, 170

[56]               References Cited

U.S. PATENT DOCUMENTS

| | | | |
|---|---|---|---|
| 3,147,749 | 9/1964 | Marsh | 600/564 |
| 3,943,916 | 3/1976 | Vadas | 600/564 |
| 3,945,117 | 3/1976 | Beaver | 30/287 |
| 3,945,375 | 3/1976 | Banko | 128/6 |
| 3,990,451 | 11/1976 | Gibbs | 128/305 |
| 4,007,732 | 2/1977 | Kvavle et al. | 128/2 |
| 4,167,943 | 9/1979 | Banko | 128/305 |
| 4,185,634 | 1/1980 | Freedman | 128/314 |
| 4,210,146 | 7/1980 | Banko | 128/305 |
| 4,221,222 | 9/1980 | Detsch | 128/305.5 |
| 4,232,676 | 11/1980 | Herczog | 128/303.14 |
| 4,248,231 | 2/1981 | Herczog et al. | 128/303.14 |
| 4,274,414 | 6/1981 | Johnson et al. | 128/305 |
| 4,368,734 | 1/1983 | Banko | 128/305 |
| 4,452,246 | 6/1984 | Bader et al. | 128/340 |
| 4,481,057 | 11/1984 | Beard | 156/216 |
| 4,485,810 | 12/1984 | Beard | 128/303.1 |
| 4,647,300 | 3/1987 | Sheets | 65/105 |
| 4,649,919 | 3/1987 | Thimsen et al. | 128/305 |
| 4,682,606 | 7/1987 | De Caprio | 600/567 |
| 4,696,667 | 9/1987 | Masch | 600/565 |
| 4,700,702 | 10/1987 | Nilsson | 128/305 |
| 4,708,138 | 11/1987 | Pazandak | 128/305 |
| 4,726,371 | 2/1988 | Gibbens | 128/305 |
| 4,754,755 | 7/1988 | Husted | 128/305 |
| 4,763,669 | 8/1988 | Jaeger | 600/564 |
| 4,774,948 | 10/1988 | Markham | 128/329 R |
| 4,798,000 | 1/1989 | Bedner et al. | 30/339 |
| 4,832,683 | 5/1989 | Idemoto et al. | 604/22 |
| 4,834,729 | 5/1989 | Sjostrom | 128/318 |
| 4,850,354 | 7/1989 | McGurk-Burleson et al. | 128/305 |
| 4,881,550 | 11/1989 | Kothe | 128/752 |
| 4,922,614 | 5/1990 | Machida | 30/339 |
| 4,943,295 | 7/1990 | Hartlaub et al. | 606/131 |
| 4,966,604 | 10/1990 | Reiss | 606/159 |
| 4,971,067 | 11/1990 | Bolduc et al. | 128/751 |
| 4,989,614 | 2/1991 | Dejter, Jr. et al. | 128/752 |
| 5,007,917 | 4/1991 | Evans | 606/170 |
| 5,026,385 | 6/1991 | Schutte et al. | 606/167 |
| 5,060,382 | 10/1991 | Wilhelm et al. | 30/244 |
| 5,071,427 | 12/1991 | Stahl | 606/172 |
| 5,074,311 | 12/1991 | Hasson | 128/754 |
| 5,111,828 | 5/1992 | Kornberg et al. | 600/567 |
| 5,112,299 | 5/1992 | Pascaloff | 604/22 |
| 5,176,695 | 1/1993 | Dulebohn | 606/170 |
| 5,183,053 | 2/1993 | Yeh et al. | 128/754 |
| 5,197,484 | 3/1993 | Kornberg et al. | 128/754 |
| 5,201,748 | 4/1993 | Newman et al. | 606/167 |
| 5,217,476 | 6/1993 | Wishinsky | 606/167 |

(List continued on next page.)

*Primary Examiner*—Max Hindenburg
*Attorney, Agent, or Firm*—Wiggin & Dana; Dale L. Carlson; Thomas F. Presson

[57]               ABSTRACT

A surgical core biopsy apparatus, having a hollow elongated member with an axis and a leading end, a sharpened edge at a portion of the leading end for cutting tissue along the axis, an actuator, and a cutting edge, linked to the actuator, being movable along a path including a transverse component to the axis, effective for severing tissue along an the path. The path is preferably an arcuate path, the cutting device being pivoted about an axis transverse to the axis of said hollow elongated member at said leading end. The actuator preferably acts by way of a compression force transmitted along the axis by a compression member, from a handle portion to the cutting edge. The elongated member is preferably a tube having two or more lumens, a first large centrally located lumen for accommodating a tissue core sample, and at least one other eccentrically located rectangular cross section lumen containing the compression member. The biopsy apparatus may be used, for example, to obtain a percutaneous excision breast biopsy from a tumor whose location is marked with a radiopaque guide wire.

25 Claims, 8 Drawing Sheets

U.S. PATENT DOCUMENTS

| | | | |
|---|---|---|---|
| 5,219,354 | 6/1993 | Choudhury et al. | 606/174 |
| 5,224,945 | 7/1993 | Pannek, Jr. | 606/159 |
| 5,226,909 | 7/1993 | Evans et al. | 606/159 |
| 5,250,063 | 10/1993 | Abidin et al. | 606/167 |
| 5,254,128 | 10/1993 | Mesa | 606/167 |
| 5,258,001 | 11/1993 | Corman | 606/167 |
| 5,269,794 | 12/1993 | Rexroth | 606/180 |
| 5,292,330 | 3/1994 | Shutt | 606/170 |
| 5,304,190 | 4/1994 | Reckelhoff et al. | 606/170 |
| 5,306,284 | 4/1994 | Agee et al. | 606/170 |
| 5,312,425 | 5/1994 | Evans et al. | 606/155 |
| 5,318,582 | 6/1994 | Chow | 606/170 |
| 5,330,460 | 7/1994 | Moss et al. | 606/155 |
| 5,346,503 | 9/1994 | Chow | 606/170 |
| 5,353,804 | 10/1994 | Kornberg et al. | 128/754 |
| 5,356,419 | 10/1994 | Chow | 606/170 |
| 5,366,468 | 11/1994 | Fucci et al. | 606/180 |
| 5,370,652 | 12/1994 | Kellan | 606/166 |
| 5,375,608 | 12/1994 | Tiefenbrun et al. | 128/754 |

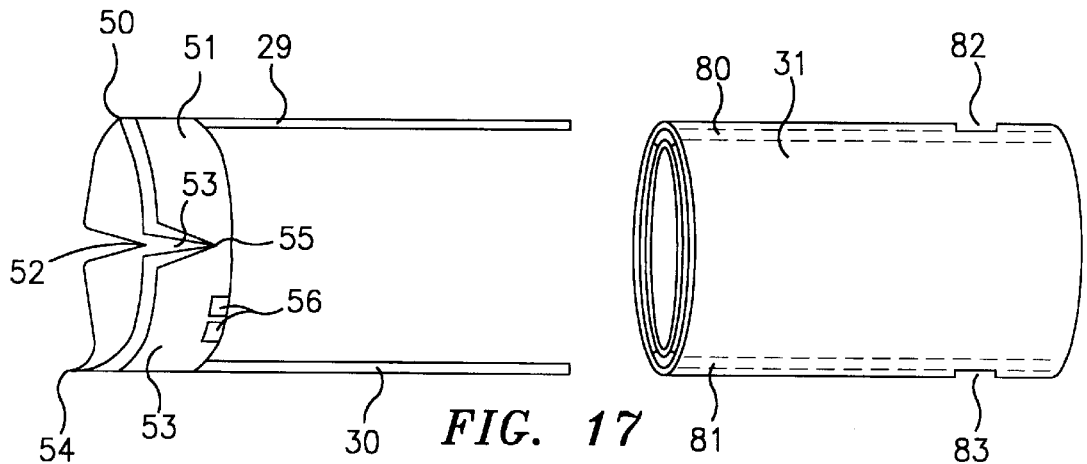
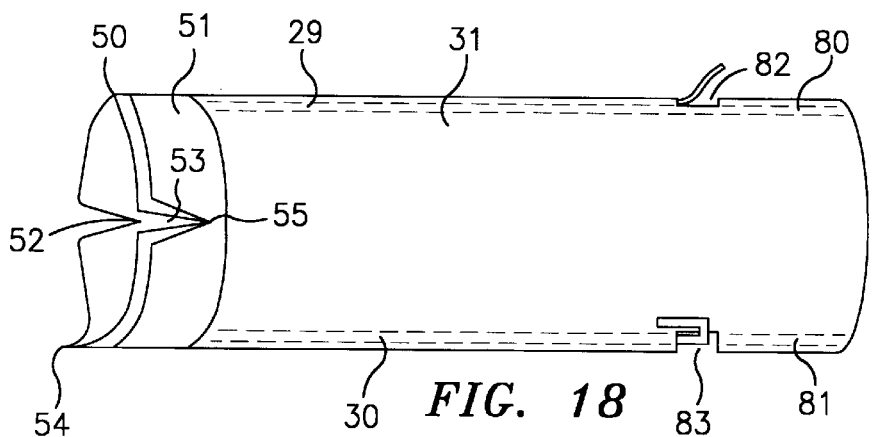
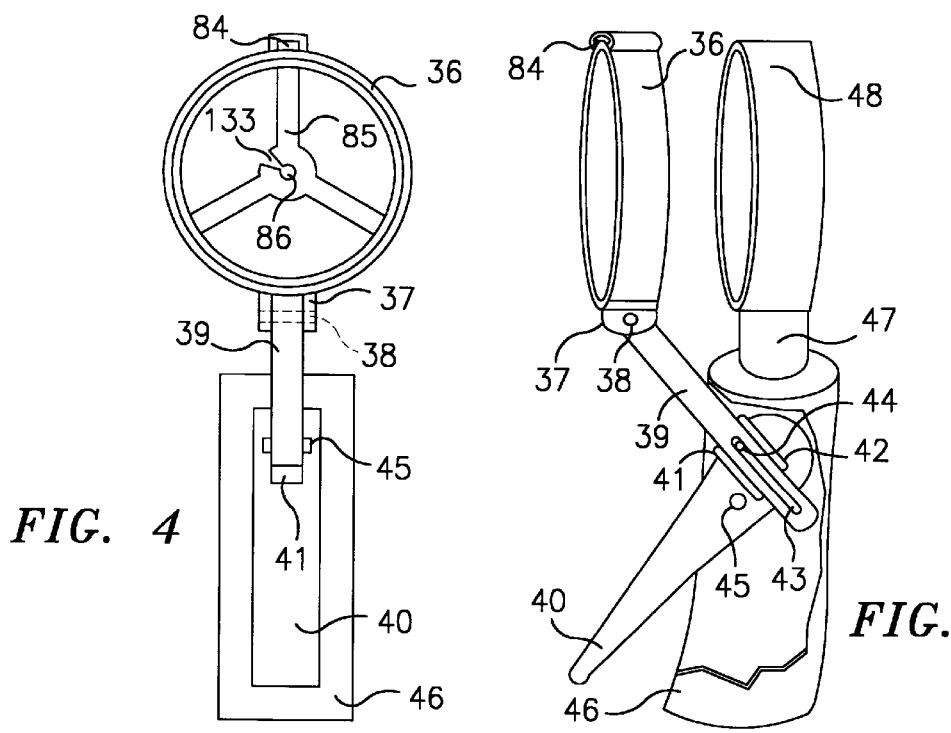

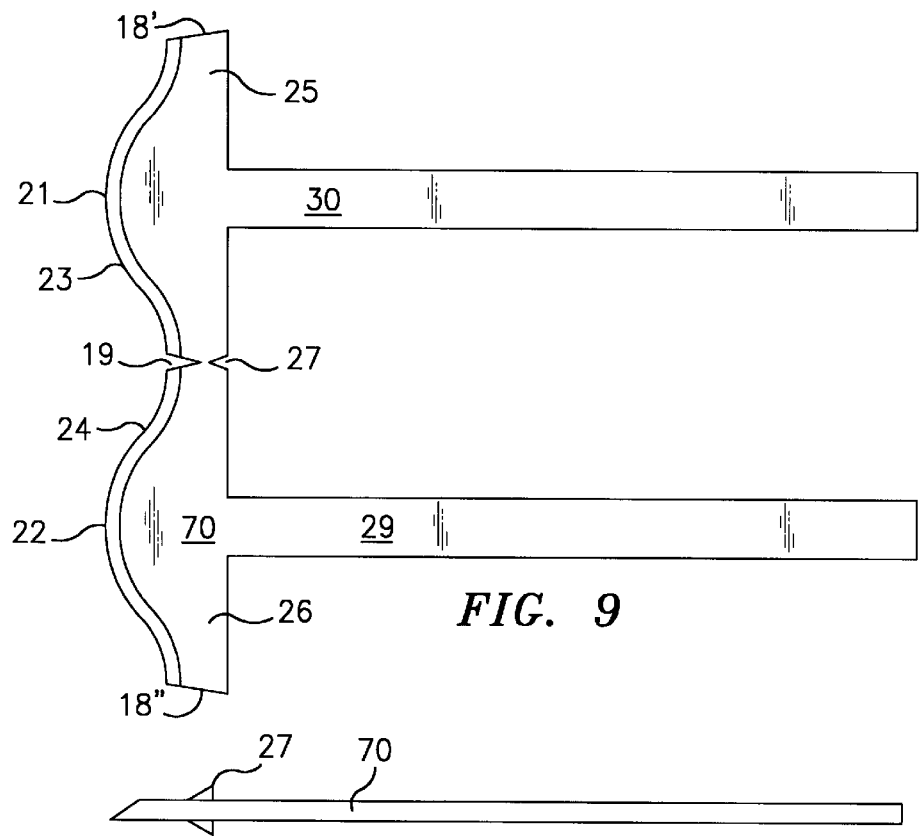
FIG. 9
FIG. 10
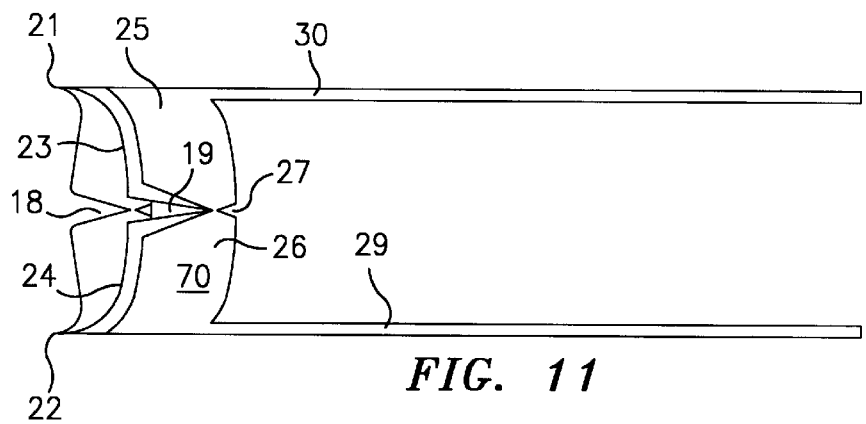
FIG. 11
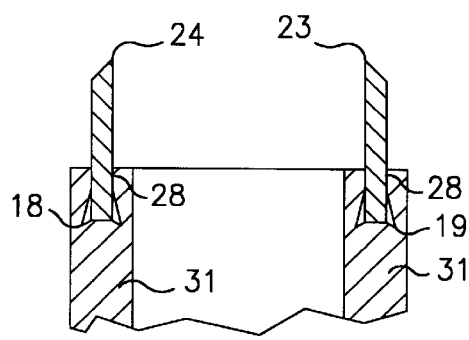
FIG. 12

SURGICAL BIOPSY DEVICE

FIELD OF THE INVENTION

The present invention relates to the field of surgical biopsy devices, and more particularly to devices intended for removal of localized breast tumors for pathological analysis.

PRIOR ART

There are many known instruments for assisting in surgical removal or sampling of tissue, for biopsy or therapy. These differ in intended situs of application, method of identifying and isolating tissue to be severed, and means for implementation. In general, tissue is sought to be cut with a sharp edge, garrotted or subjected to localized shear forces, although tearing, aspiration, electrosurgical and other methods are known.

U.S. Pat. No. 4,007,732 relates to a method for location and removal of soft tissue in human biopsy operations. A guide wire is placed radiologically for removal during a biopsy procedure. A separate knife is employed in order to sever the core biopsy sample. U.S. Pat. No. 5,375,608 relates to a core biopsy device having a cutting blade which operates transverse to the axis of insertion. U.S. Pat. No. 5,074,311 relates to a core biopsy device having severing blades which are activated by a tension on an actuator.

U.S. Pat. No. 4,971,067 relates to disposable biopsy instrument having two jaws which sever a tissue sample by a shearing action.

U.S. Pat. No. 4,774,948 relates to a device for inserting a guide wire having a distal barb.

U.S. Pat. No. 5,111,828, U.S. Pat. No. 5,197,484 and U.S. Pat. No. 5,353,804, incorporated herein by reference, relate to methods and devices for percutaneous excision breast biopsy (PEBB) of a mass localized by a guide wire. A garrotte is employed to sever the core of breast tissue.

U.S. Pat. No. 4,881,550 relates to a surgical cutting forceps or biopsy instrument having two hinged cutting blades, which are actuated by the movement of a concentric sleeve about a central body. This device is not intended for taking core biopsies.

U.S. Pat. No. 5,366,468, U.S. Pat. No. 5,112,299, U.S. Pat. No. 4,834,729, U.S. Pat. No. 4,850,354, U.S. Pat. No. 4,754,755, U.S. Pat. No. 4,368,734, U.S. Pat. No. 4,274,414, U.S. Pat. No. 4,167,943 relate to surgical instruments having an axially rotating cutting blade which cooperates with a concentric sleeve to cut using a shearing action. U.S. Pat. No. 5,312,425, U.S. Pat. No. 5,226,909, U.S. Pat. No. 5,007,917, U.S. Pat. No. 4,649,919 and U.S. Pat. No. 3,945,375 relate to surgical instruments having a helically twisted blade which rotates within a sleeve to cut tissue. U.S. Pat. No. 5,269,794 relates to a rotating blade arthroscopic surgical instrument. U.S. Pat. No. 5,224,945 and U.S. Pat. No. 4,966,604 relate to expandable arthrectomy cutters.

U.S. Pat. No. 4,210,146 relates to a surgical device which has two sharpened members which move with respect to each other for shearing. U.S. Pat. No. 5,219,354 relates to a combined dissecting and hemostapling scissors. U.S. Pat. No. 4,452,246, U.S. Pat. No. 4,726,371 relate to scissors apparatus for cutting tissue. U.S. Pat. No. 5,060,382 relates to a cutting shears.

U.S. Pat. No. 3,945,117, U.S. Pat. No. 4,185,634, U.S. Pat. No. 4,647,300, U.S. Pat. No. 4,708,138, U.S. Pat. No. 4,798,000, U.S. Pat. No. 4,922,614, U.S. Pat. No. 5,026,385, U.S. Pat. No. 5,071,427, U.S. Pat. No. 5,201,748, U.S. Pat. No. 5,217,476, U.S. Pat. No. 5,250,063, U.S. Pat. No. 5,254,128, U.S. Pat. No. 5,258,001, U.S. Pat. No. 5,292,330, U.S. Pat. No. 5,318,582, U.S. Pat. No. 5,346,503, U.S. Pat. No. 5,356,419, U.S. Pat. No. 5,370,652 relate to sharp bladed cutting instruments. U.S. Pat. No. 5,304,190 and U.S. Pat. No. 5,176,695 relate to endoscopic sharp bladed cutting instruments for severing tissue. U.S. Pat. No. 5,306,284 relates to an endoscopic cutting instrument having visualization capability. U.S. Pat. No. 4,700,702 relates to a surgical cutting device having a moving band cutting blade. U.S. Pat. No. 4,221,222 relates to a surgical tissue shaving device for obtaining planar tissue samples. U.S. Pat. No. 4,943,295 relates to a flexible bladed cutting instrument.

U.S. Pat. No. 4,832,683, U.S. Pat. No. 4,485,810, U.S. Pat. No. 4,481,057, U.S. Pat. No. 4,248,231, U.S. Pat. No. 4,232,676 relate to electrically assisted surgical cutting devices.

U.S. Pat. No. 3,990,451 relates to a biopsy device for obtaining a tissue sample core. U.S. Pat. No. 5,183,053 relates to an elliptical biopsy punch.

U.S. Pat. No. 4,989,614 relates to fine-needle aspiration cell sampling methods. The device is not intended for obtaining a core tissue sample.

BACKGROUND OF THE INVENTION

Many devices are available for the surgical removal of tissue. These devices are generally characterized as having sharp cutting blades, which sever tissue by means of a sharpened edge, having an angle of 5–30 degrees to the plane of cutting. These blades cut by applying pressure along the plane of cutting, forcing the tissue against the blade, severing connective tissue. Another system for severing tissue is a scissors, in which two edges move with respect to each other to shear the tissue. The edges generally are sharpened at an angle of 90–45 degrees from the plane of cutting. The actual cutting with a scissors occurs at the junction of the edges, which moves outward from a pivot point of the two edges as the scissor is closed. The relative motion between the two edges produces a shear force with separates the tissue. Electrosurgical methods are also known. Biopsy devices may also be implemented by blunt pressure or tension.

Another method of severing tissue is known as the garrotte method in which a thread or thin wire is formed in a loop, and the diameter of the loop is decreased, cutting through the tissue inside the loop. When used to sever a biopsy sample, a sharpened circular blade is used to place the garotte at the desired tissue depth.

It is generally desirable that biopsy devices remove the entirety of a small solid tumor in a single procedure, in order to prevent possible tumor cell seeding and to effectively remove a primary source of tumor cells. This also allows pathological examination of tumor margins. Further, it is desirable to provide a biopsy device in which tissue contact portions are disposable, in order to eliminate the possibility of cross infection of patients. However, known biopsy instruments generally are of expensive and durable construction, and may not be cost effective for single use.

It is desired that biopsy instruments be easily guided to the situs of a target area, which is generally identified radiologically, ultrasonically or in another manner. Therefore, one known technique is to insert a guide wire into a target area in a visualization procedure. Thereafter, a biopsy instrument is fed along the guide wire, and a biopsy is taken to include the tissue around the end of the guide wire. The biopsy device may also be directly guided to sample to target area using standard guiding techniques, such as ultrasonography, fluoroscopy or digital fluoroscopy.

Mechanisms are known for converting a linear movement of an actuator to a pivotal movement of a member about an axis. Known biopsy forceps include a mechanism for converting a linear trigger movement to a movement of two cups toward each other, to grasp and sever tissue. The cutting edges of traditional biopsy cup forceps are generally scissor-type cutting devices, shearing rather than cutting tissue.

A known guide wire system is the "Sadowsky Breast Marking System" (TM) (catalog # SBS-10, SBS-5) by Ranfac Corp., Avon Mass. This system facilitates insertion of a guide wire in a breast, and includes three basic elements. First, a 9 inch guide wire 0.010" diameter (spring hook wire), having a flattened spiral portion with a 3 cm pitch, an etched marking at 10 cm, and a sharp kink at one end with a 345° bend at one end with an 8 mm tail. A 23G stiffening cannula, approximately 4–6 cm long with etched markings at 1 and 2 cm from the end is provided, which has a central aperture for the guide wire. Finally, a 20G×10 cm or 20G×5 cm needle with centimeter markings is provided, through which the guide wire is inserted. In use, a lesion is located by mammography. An insertion path is selected at the discretion of the surgeon, generally minimizing the path of the guide wire through the breast tissue, though the angle should generally be parallel to the chest wall to avoid complications such as pneumothorax. The needle, without the guide wire, is then inserted to the desired depth which may be, e.g., 1 cm beyond the radiographic margin of the lesion. The guide wire is then inserted through the needle until the etched marking disappears into the needle, thus releasing and engaging the hook of the needle. The needle is then withdrawn over the guide wire, leaving the guide wire in place. Further radiographs are taken to ensure that the wire passes through the lesion, and an appropriate length stiffening cannula is placed over the guide wire, so that the tip of the stiffening cannula is at the location of the lesion. The stiffening cannula also prevents accidental bisection of the guide wire. After excision, the surgical biopsy specimen may be radiographed to ensure that the lesion is within the biopsy sample.

SUMMARY AND OBJECTS OF THE INVENTION

The present invention provides a biopsy device which provides a sharp knife-type cutting system to sever selected tissue with a circular blade which swings around a pivot.

A means for placement of a guide wire is employed, using standard techniques, to insert a guide wire in and through target tissue, which may be a tumor, suspected tumor, or other tissue of interest. The device provides means for following the guide wire placed in the tissue target, so that assurance may be had that the tissue of interest is being removed.

The device has a low cost design, and therefore is suitable for use as a disposable instrument. The cutting edge is blade sharp, and is preferably provided with integral extensions for affixing the blade to the device during assembly.

The device creates a core around and including the tissue of interest, and advantageously, the cutting edge for severing the tissue core is integral with a cutting edge for inserting the biopsy device along the guide wire to create the core, with an integral hinge portion linking the two. Therefore, a trifunctional element is preferably provided, which (a) bores deep into the tissue to the level of the biopsy location, (b) hinges the cutting edge so that it may pivot to sever the bored biopsy specimen and (c) severs the biopsy specimen from the patient. A means is also preferably provided to retain the tissue core biopsy in the body of the instrument during withdrawal from the patient. Thus, a forward cutting edge, a hinge and a lateral cutting edge are provided. Of course, the hinge need not be integral to the cutting elements, and may be provided as a separate element, such as diametrically positioned pins or rivets.

The device is constructed having a number of portions having specific functions. A handle is provided which is ergonomically designed to be held in the hand of the surgeon, with one or more fingers free for manipulation of the activation device. The handle may be any suitable material, such as a thermoformable plastic, e.g., ABS, or other plastic. The handle may also be formed of stainless steel, aluminum, or other metal. The handle is provided as an elongated member that rests in the palm of the surgeon's hand. The handle is provided to support the biopsy device, and to allow the surgeon to applying pressure axially along an elongated tubular member to bore the biopsy device to the desired location along the guide wire. The handle also has a related manual actuator, for actuating the severing device.

An actuator is provided in proximity to the handle, or may be a part of or integral to the handle. The actuator may be, for example, a trigger or depressible element which is compressed by the surgeon's fingers against the handle. It is preferred that this trigger be positioned at the front of the handle, so that pressure applied to the rear of the handle causes the device to be inserted into the patient, without accidental activation of the actuator. Other types of actuators may be used, for example, other types of mechanical actions, hydraulic, pneumatic, electrical or electronic, and other known types. The actuator may also be activated by the surgeon's free hand, as a separate element from the handle. The actuator, either directly or indirectly, when actuated, causes the cutting edge, which is semicircular, to pivot about an axis passing through the two ends of the cutting edge, which is disposed perpendicular to the axis of the elongated tubular member.

Thus, in a preferred embodiment, a member slides under compression to directly urge a portion of the cutting edge, spaced from the pivot points on the pivot axis, to apply a torque about the pivot axis, thereby swinging the cutting device through an arc to sever the tissue. In another embodiment, two cutting edges are provided which each swing through an arc to sever the tissue, meeting at a central position in front of the device.

The actuator acts through a force transmission system, such as the sliding member described above. The sliding member, or a portion thereof, may be integral to the cutting device, formed of a thin flexible steel strip. As noted above, the force transmission system may also be of other types, including other mechanical linkages, hydraulic, pneumatic, electromechanical or electronic.

Another possible linkage type includes a tension element which acts on a portion of the cutting device distal from the pivot point and opposite to the cutting edge from the pivot axis, thus applying a torque to cause outward rotation of the cutting device, cutting edge first, about the pivot axis to sever the tissue.

In a device having a compression linked strip, the strip may slide in a space within the wall of the elongated member, preventing buckling of the strip under pressure and leaving the center of the elongated member open and unobstructed to receive the tissue core. According to alternate embodiments, tension devices, hydraulic or pneumatic lines or electrical wires may also be provided in a wall of the elongated member in order to transmit the actuation signal to the biopsy device cutting system.

The elongated tubular member extends away from the handle. The elongated member is preferably a thin walled tube, of predetermined length, preferably between about 6 and 12 inches long. A variable length telescoping embodiment is also possible, with an adjustable actuator linkage system to compensate for the adjustable length between the trigger and the cutting edge. The preferred material is plastic, more preferably a rigid thermoplastic.

When a compression force transmission member is housed in the wall, the elongated member is preferably formed as an extruded dual or triple lumen tube, with a central round cross section aperture, and a thin wall with one or more eccentric rectangular cross section lumens. The elongated tubular member may also be formed of other types of plastic, metal, glass or ceramic. The round central aperture in the elongated tubular member allows the bored tissue to be trapped as a core within the elongated member, thus preserving the anatomical relation of the tissues and preventing disruption, facilitating pathological study. Further, it is believed by some that if a tumor is localized, limited manipulation during biopsy can reduce the risk of tumor seeding.

After the biopsy procedure, the instrument may be subjected to radiological inspection or by other means to ensure that the identified suspect tissue is contained within the device. Likewise, a post biopsy examination of the patient may ensure that the suspect tissue has been biopsied. Intraprocedural imaging may also be used to confirm localization prior to severing the tissue sample.

In a further embodiment, alternately or in addition to a guide wire, the area of suspect tissue may be marked to enhance its visualization by another technique, for example by injection of a radiopaque dye for radiological localization, injection of microspheres for ultrasonic localization, injection of magnetic particles for magnetic localization, and other known techniques. Therefore, a localization transducer system may be coupled to the biopsy instrument for intraprocedural localization. A sensor system may also be provided in conjunction with the device to warn the surgeon or contact or potential contact between the cutting edge and the guide wire.

In a one embodiment, the biopsy device, with the exception of the cutting edges and the force transmission system, are formed of radiotransparent materials, so that the location of the suspect tissue can be confirmed, if desired, prior to removal. Materials might also be employed which allow the entire biopsy device to be substantially radiotransparent or radiolucent, with the possible exception of a radiographic indicator, and such a device is within the intended scope of the present invention. The tissue core may then also be radiographed within the biopsy device after removal from the patient.

According to the present invention, a radiological apparatus is not necessary to conduct the biopsy, and may replaced, e.g., entirely by ultrasonic apparatus. This is desirable, for example, for outpatient or surgical office procedures. In this case, the guide wire preferably has ultrasonic markers, e.g., gas filled portions, at or near the barbed tip and at a distance away from the tip, so that the guide wire may be inserted and localized accurately under ultrasonic guidance. Ultrasonography may also be used intraprocedurally to ensure accurate placement of the biopsy instrument.

Alternate to an integral multilumen tube, the elongated tubular member may also be formed as a composite structure of cylindrical shells with spacing elements, in order to form a desired multilumen structure. Thus, outer and inner tubular shells spaced with two curved sheets forms a cylindrical member having a large central lumen and two separated lumens in the composite wall.

According to another embodiment of the present invention, a plurality of biopsy tissue samples may be obtained sequentially, and held in separate compartments within the elongated member, separated by septa. A septum may be formed by an apertured elastic membrane which selectively allows a tissue sample to pass through the aperture under pressure or vacuum, and thereafter retains it in place by the elastic force of the septum material. The design of the instrument allows a controlled unidirectional force to be applied, which moves a tissue specimen from a distal compartment to a proximal compartment. A mechanism may also be provided to selectively open and close the septa, e.g., a pursestring mechanism, thereby reducing the force necessary in order to transfer tissue samples from one compartment to the next. The force for positioning the core sample in desired chambers may be a mechanically applied force, pushing the tissue core proximally, or a pneumatic force, from a compressed gas or vacuum line, or both. A wire barb may also be used to apply traction to tissue sample. Such a multi-sample biopsy device is advantageous for, e.g., endoscopic application to avoid removal the device between samples.

The distal end of the elongated tubular member includes a boring edge, which is sharp, and cuts through tissue with slight pressure or pressure in combination with a twisting or rotating action. The preferred configuration is a curved steel sharpened blade, conforming to the shape of the elongated tubular member and extending from a distal edge thereof, having a central lobe extending further distal than the remainder, tapering proximally on both sides. The boring edge extends approximately one half of the circumference of the elongated member, and is fixed in place with respect to the elongated member. As the elongated tubular member is pressed forward, the central lobe cuts the tissue. The tapered portions are inclined to the force vector, and therefore tend to slice through the tissue. As the elongated member is rotated, e.g., ±90°, the tissue around the entire biopsy device is severed, and a core defined. Thus, the elongated member is able to advance through the tissue with a core accumulating within the central aperture of the elongated tubular member. It is noted that during insertion, both the boring edge and the cutting edge are aligned with the longitudinal axis of the elongated member, so that a sharp edge is presented around essentially the entire elongated member.

During a procedure, a guide wire is radiologically, ultrasonically or otherwise located to extend through and/or beyond a tumor or tissue to be biopsied, along an axis for providing tissue access. For example, a calcified tissue mass of about 1 cm diameter may be identified radiologically. In a preliminary procedure, a guide wire, having a distal barb, is inserted along an axis along which a later biopsy incision is to be made, so that the guide wire extends through the middle of the suspect tissue, with the barbed tip extending a short distance beyond the suspect tissue. The surgeon then makes a skin incision including the access axis, and dissects along the access axis some distance into the breast tissue, a safe distance from the suspect tissue.

The guide wire is then fed into the elongated tubular member of the device and a distal portion thereof linked to a retaining device which guides the biopsy device centered on the guide wire. The guide wire is marked in relation to the biopsy device, so that when the guide wire obtains a particular relation to the biopsy device, which is determined by markings or a positioning means, the barb is within the aperture of or in desired relation to the elongated tubular member.

After the tip of the biopsy device is located to the desires of the surgeon, the actuation device is activated, which causes the force transmission device to swing the cutting member or members about a pivot axis, to sever the tissue. The guide wire is secured by the surgeon against movement, and may be simultaneously tugged slightly, for example about 0.25 lbs. force, in order to ensure that the tip of the guide wire is safely within the swing arc of the cutting member. The cutting member swings an arc to essentially meet the boring edge, fully severing the tissue core. In another embodiment, two opposing edges pivot toward each other, and meet in a central location, severing the tissue core.

The pivot element includes a portion fixed to the elongated tubular member, and a portion which either flexes or rotates about an pivot axis, e.g., a rivet or pin. A flexion-type hinge is preferred, allowing the cutting edge and boring edge to be integral.

In a preferred embodiment, a single thin steel sheet stamping to form the cutting and boring edges is provided, having two portions, a first portion having a sharpened boring edge having a convex central lobe tapering laterally, and means proximal to the boring edge for firmly engaging to the elongated tubular member, such as a crimped edge, with is forced into a circular counterbored groove in the distal edge of the elongated tubular member. Where the tubular member is a composite structure, the inner and outer shells extend beyond the spacers to provide a gap for engaging the affixed edge of the boring member portion. The second portion is provided adjacent the first portion, having a linear sharpened cutting edge. Bridging the boring edge and the cutting edge, i.e., the first portion and the second portion, is a narrowed portion, with a "V" notch, to allow flexion in the plane of the sheet with low applied force. In the center of the side including the cutting edge, a narrow strip extends a distance away from the cutting edge, being of about equal length to that of the elongated member, or somewhat longer, and which therefore bridges the actuator with the cutting edge. The portion including the cutting edge has, opposite the "V" notch, a portion which acts as a hinge with its opposite counterpart, i.e., the lateralmost edges of the first and second portions, and is held in the counterbored groove or circular recess. The narrow strip is inserted into an aperture in the wall of the elongated member, through which it slides without buckling. The cutting edge and the boring edge are sharpened to razor sharpness using standard methods.

Instead of the flexion hinge between the first and second portions, the cutting edge and boring edge may be provided on separate members which are hinged on opposite sides of the tip of the elongated member.

According to known principles, the cutting edge or the boring edge may be electrosurgical devices. Thus, either or both of these blades may include heating elements (see U.S. Pat. No. 4,481,057, U.S. Pat. No. 4,485,810), vibrating elements (see U.S. Pat. No. 4,832,683), electrocautery elements (see U.S. Pat. No. 4,232,676, incorporated herein by reference), or electrosurgical cutting elements (see U.S. Pat. No. 4,248,231). In these cases, the blade is formed in accordance with this additional functionality as is known in the art. For example, the biopsy device may be configured with a selective electrocautery device which reduces hemorrhaging from the cut tissue edges. When employed, it is preferable that the system be arranged so that the electrocautery is applied in such manner that the biopsy sample is not adversely affected by the electrical currents, facilitating histological and pathological analysis of the tissue sample. Therefore, the electrocautery may be applied after the sample is safely inside the central aperture of the elongated member, in a secondary removal procedure. The cutting edge may therefore be provided with a leading cutting edge to sever the core biopsy sample, and a trailing electrocautery edge, to cauterize the tissue as the trailing edge passes the fresh cut tissue. Alternatively, the cutting edge may cauterize during a backswing chase from a fully extended position to a resting position. An electrocautery member near the distal edge of the boring edge or on the outer wall of the elongated member may also be activated upon device removal.

In operation, the cutting edge need not return to the open position, and may be locked in the fully extended position. The trailing edge of the cutting edge blade may include an extensible sheath, which provides a barrier to retain the tissue sample. In this event, it is preferred that the sheath be formed of an elastic silicone, latex or other rubber compound, and that the cutting edge terminate its swing arc concentrically inside the boring edge, and be retained in this position during instrument withdrawal. A spun, knit or woven cloth or coated cloth may also be employed as a sheath.

The boring and cutting edges may be recessed within the wall or in the lumen of the tubular member when not being used, and extended when boring or cutting is required. This mechanism may either retract the members having sharp edges or extend the tubular member, or portions thereof, with respect to the sharp edges. Thus, during handling prior and subsequent to the procedure, safety is enhanced. Further, after the biopsy device is inserted to an appropriate depth in the patient, the boring edge may be disengaged to prevent further insertion or adverse effects from accidental jarring.

The biopsy instrument according to the present invention may also include or be used in conjunction with optical elements, such as illumination elements, e.g., incandescent bulb, LEDs, fiber optics; laser surgical apparatus; video camera apparatus, fiber optic or standard optic endoscopic apparatus; or other known surgical optical devices. See U.S. Pat. No. 5,306,284. For example, through the elongated tubular member, a light source may be provided to enhance visualization through the central aperture during the biopsy procedure, and an endoscope provided to transmit the image from near the tip of the device to the surgeon.

The biopsy instrument according to the present invention may also include ultrasonic, radiographic, optical, magnetic, or other type of localization system, in order to assist in guiding the instrument to the site of the lesion or suspected tumor, or to allow visualization of the tissue within, surrounding or in front of the biopsy instrument. For example, an ultrasonic transponder system may be provided to determine the location of an echogenic guide wire or stiffening cannula, or to locate the suspected tumor or lesion itself.

It is therefore an object according to the present invention to provide a biopsy device for taking a core biopsy, having a sharpened leading edge for cutting the tissue to obtain the core, and a pivoted cutting edge for severing the core tissue biopsy from the body.

It is a further object according to the present invention to provide a biopsy instrument suitable for one time use having a simple construction with a sharp cutting edge.

It is a still further object according to the present invention to provide a guide wire located biopsy device having a pivoting cutting device.

The present method also provides a method for taking a tissue biopsy by inserting a guide wire, dissecting around the guide wire, placing a coring biopsy device along the guide wire beyond the suspect tissue, and severing the core tissue sample using a pivoting semicircular blade.

These and other object will become apparent through a review of the detailed description of the preferred embodiment with reference to the drawings.

BRIEF DESCRIPTION OF THE DRAWINGS

The preferred embodiments of the invention will now be described with respect to the drawings, in which:

FIG. 4 shows a front view of an instrument according to the present invention, having a star-shaped centering device for guiding the instrument with respect to the guide wire;

FIGS. 9, 10 and 11 show a blade member according to a first embodiment of the present invention having dual lobed blades, in top, side and folded views, respectively;

FIG. 12 shows the folded blade of FIG. 11, having expanded retaining portions;

FIG. 17 shows the folded blade of FIG. 15 juxtaposed for insertion into the tube according to FIG. 5;

FIG. 18 shows the folded blade and tube of FIG. 17 in inserted position; and

FIG. 19 shows a perspective view of a handle and actuator system of the present invention.

Figure 1A:
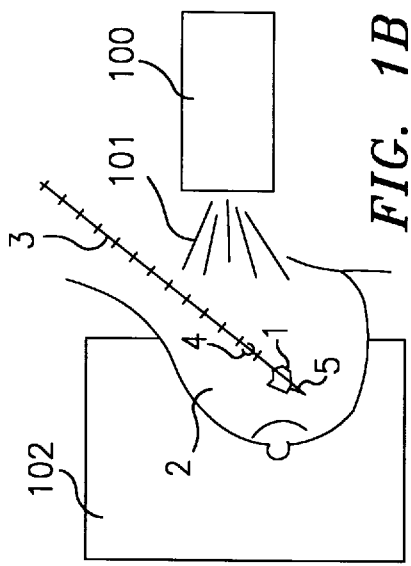
FIG. 1A shows a breast having a suspected tumor.
Figure 1B:
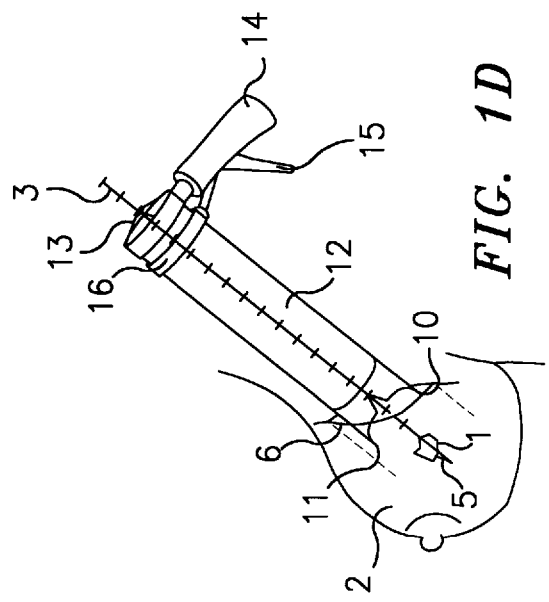
FIG. 1B shows a breast with a guide wire inserted through the suspected tumor.
Figure 1C:
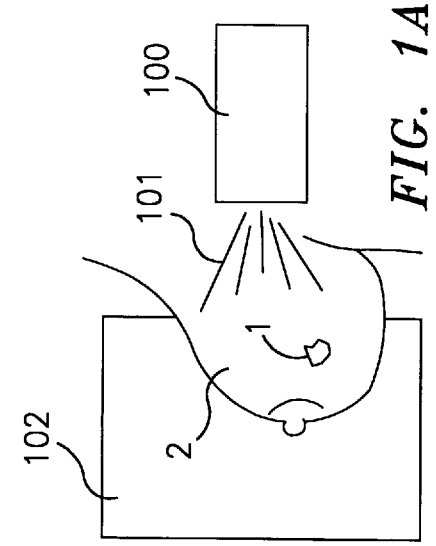
FIG. 1C shows a breast with a skin incision and a guide wire inserted through a suspected tumor.
Figure 1D:
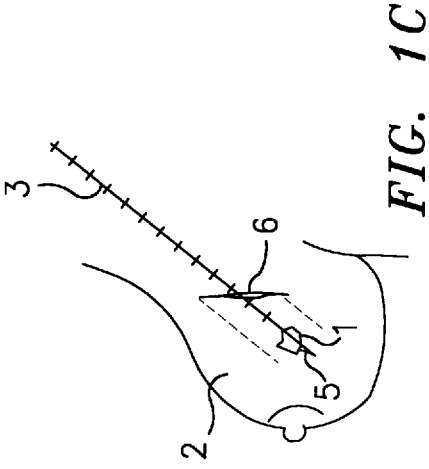
FIG. 1D shows a biopsy instrument according to the present invention inserted coaxially with a guide wire for biopsy of s suspected tumor.
Figure 1E:
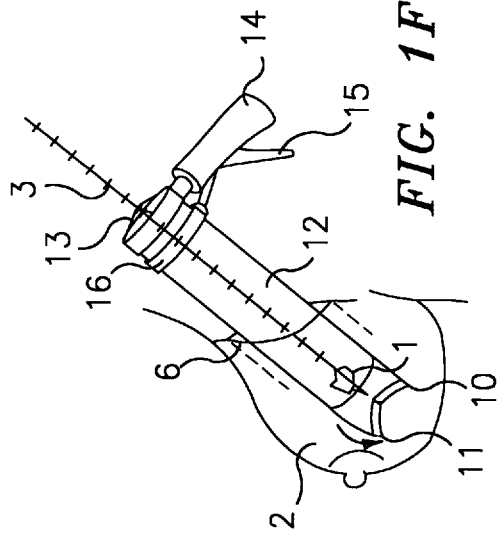
FIG. 1E shows the instrument as shown in FIG. 1D inserted further coaxially over the guide wire to encircle the suspected tumor.
Figure 1F:
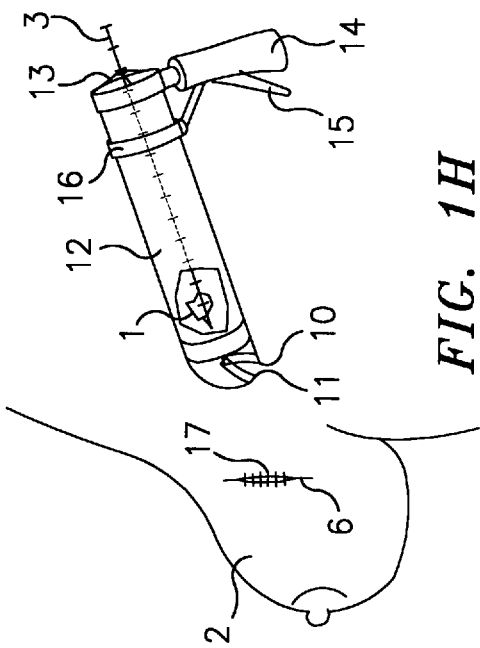
FIG. 1F shows the instrument as shown in FIG. 1E during an initial stage of actuation for severing the tissue core sample including the suspected tumor.
Figure 1G:
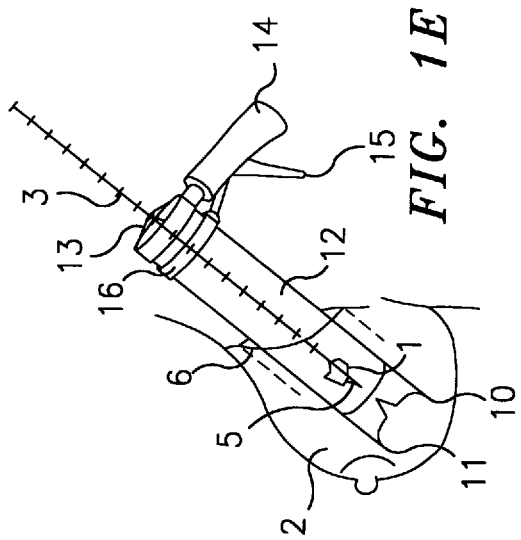
FIG. 1G shows the instrument as shown in FIG. 1F at the conclusion of the actuation, after severing the tissue core sample including the suspected tumor.
Figure 1H:
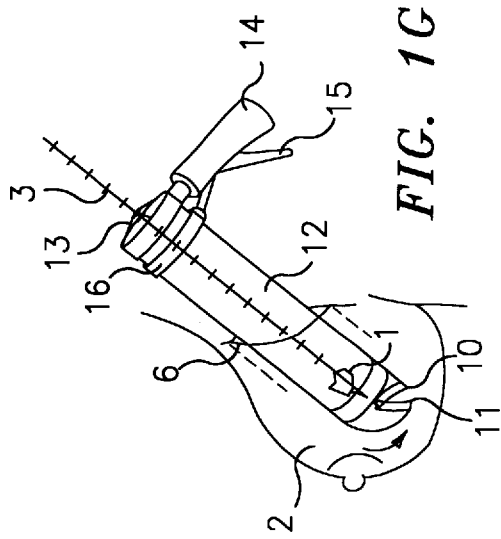
FIG. 1H shows the instrument as shown in FIG. 1G, removed from the breast with the suspected tumor in a tissue core sample contained therein, with the skin incision closed using sutures.

It should be noted that these Figures are not drawn to scale, and the relative dimensions and proportions of some parts have been greatly exaggerated or reduced for the sake of clarity and convenience in the drawing. Furthermore, some parts of the cryogenic radiation detector which it are not necessary to describe for an understanding of how to perform the present invention have not been shown in the drawings, but may be provided in known manner.

DETAILED DESCRIPTION OF THE PREFERRED EMBODIMENTS

EXAMPLE 1

A surgical biopsy device is provided for use in breast biopsy for tissue sampling of selected areas. Using state of the art mammography techniques, suspect tissue 1, e.g., tumors or other localized tissue anomalies may be detected which are smaller than 1 cm diameter. In general, tumors up to about 2 cm are suitable for biopsy with simple tools, while significantly larger tumors may require a lumpectomy or other type of procedure in order to adequately obtain the tissue sample and avoid the need for a subsequent procedure, even if the tumor is not malignant. Thus, the biopsy device includes a system for obtaining a core biopsy sample of sufficient size to encircle a suspect area. Thus, a circular cutting edge is provided at the leading edge of a tubular biopsy instrument.

Because, in the general case, the suspect tissue is identified or confirmed radiologically, its location may be verified radiologically, or by ultrasound or other method. As shown in FIGS. 1A–1H, in a fluoroscopic procedure, a standard type of specially adapted radiopaque guide wire 3 is inserted along a surgical biopsy axis, through the center of the suspect tissue 1, with a barbed retaining portion 5 extending a short marginal distance beyond the suspect tissue 1. An X-ray source 100 emits X-rays 101, which are received by an X-ray detector 102, to visualize the suspect tissue 1, in the breast 2, simultaneously with the guide wire 3, to accurately position the barb 5 beyond the suspect tissue 1 along a desired axis. Where ultrasound or other technique is employed to localize the guide wire 3, the guide wire 3 is provided with a detectable property for that localization method to allow simultaneous detection of the location of the suspect tissue 1 and the guide wire 3 for simple confirmation of placement. Of course, it is also possible to use different localization methods for the suspect tissue 1 and the guide wire 3 and employ a correlation system to correlate the respective locations.

The biopsy instrument is inserted with the guide wire 3 centrally placed along the axis of the tubular shaft 12 of the biopsy device. Centering devices 13 may be provided to self-center the guide wire 3 within the biopsy device. For example, one or more inserts 85, shown in FIG. 4, pressed against the inner wall of the tubular shaft 31, with a small central aperture 86 for the guide wire 3 may be provided. The aperture is optionally adjacent to a "V" shaped groove 133 to facilitate positioning of the guide wire 3 in the aperture 86. These may be fixed in place, or adapted to slide within the tube. The elongated tubular member 31 may also have an open end near the handle 46, so that the device may also be sight guided to the suspect tissue 1 site.

When the biopsy device is in position, the actuator 40, which is in the form of a trigger, e.g., a finger operated depressible member, is depressed, causing a force transmission element, e.g., a sliding steel member 29 in a rectangular second aperture within the wall of the tube, to slide distally. This sliding steel member 29 is fixed to a circular slide 36 by a clamp 84. The sliding steel member 29 is contained within the second lumen 80, so that it cannot buckle, exiting at aperture 82. The sliding steel member 29 is stiff enough so that it does not buckle in the region beyond the end of the tube 31, yet elastic enough that it is flexible. The sliding steel member 29 forces the steel cutting edge 51, 50 forward. The sliding steel member 29 is preferably integral with the steel cutting edge 51, 50, and linked in the central portion 55. The steel cutting edge 51, 50 is pivoted at two diametrically spaced pivot points 55, 52 about the end of the tube 31. Therefore, the pressure of the sliding steel member 29 causes the steel cutting edge 51, 50 to swing in an arc about the pivot points 55, 52. The sliding steel member 29 flexes along the arc of the steel cutting edge 51, 50.

The guide wire 3 preferably is marked or demarcated at critical lengths, so that it can be reliably verified when the apex of the arc of the cutting edge 51, 50 is beyond the end of the guide wire 3. Thus, the guide wire 3 may have a device at a fixed length from the tip, which is adapted for cooperation to the biopsy device, so that the relation may be determined by mechanical, electrical or other automated means. Otherwise, a visual indicator may be provided for visual confirmation of the relative placement of the guide wire 3 and the biopsy device. Preferably, a mechanical link of the insert 85 is provided in a portion of the elongated tubular member 31 near the handle 46. During the cutting by the cutting edge 50, a slight retraction is provided on the guide wire 3, of sufficient force to stabilize the guide wire 3 and to allow the instrument to advance, assisting the tissue core into the elongated tubular member 31, yet small of small enough magnitude not to disturb the placement of the barb 5 within the tissue. Thus, after the tissue core sample is severed, it is contained within the elongated tubular member.

After the tissue is severed, the biopsy device is removed. Standard techniques are then employed to close the wound, such as sutures 17 and provide the necessary hemostasis.

EXAMPLE 2

The biopsy device is constructed as a triple lumen elongated tubular member 31 formed of polycarbonate plastic. The tube has an ID of 2.5 cm, with a wall thickness of 2 mm. Within one portion of the wall, the second lumen is provided as a 1 mm thick, 4 mm wide rectangular opening, into which the sliding steel member 29 fits. If necessary, the sliding steel member 29 may be treated with an acceptable lubricating material, such as a PTFE film, in order to prevent binding within the sliding path of the lumen 80.

An ergonomically designed handle 46 is provided attached to the elongated tubular member 31, so that the elongated tubular member 31 is parallel to the arm of the surgeon when the handle 46 is held in the surgeon's hand. A trigger actuator 40 is attached in front of the handle 46, so that it is depressible by the surgeon's fingers. The trigger actuator 40 is attached to the sliding steel member 29 by the clamp 84 on a circular sleeve 36 which rides outside the elongated tubular member 31, so that a depression of the trigger 40 against the handle 46 causes the sliding steel member 29 to extend distally within the sliding path of the lumen 80, toward the tip of the device.

With the configuration described, the sliding steel member 29 must move approximately ½ πD (0.5×3.14×2.5) or 3.9 cm. Of course, this distance depends on the size and configuration of the instrument, and will vary accordingly. This movement is provided by direct action of an arm 39 linked to the trigger actuator 40 about a pivot axis 45, or a compound machine for multiplying the distance moved by the trigger, thus reducing the required trigger travel. The arm 39 slides between two guides 41, 42, and is held to the trigger actuator 40 by a pin 44 which rides in a groove 43. The arm 39 is linked by a pivot pin 38 on an extension 37 of the circular sleeve 36.

The trigger may be provided with a system to ensure that the cutting edge is not accidentally actuated, and after actuation it is reliably and full), actuated. Thus, a ratchet which does not allow the trigger to return to resting position until fully depressed, or another type mechanism may be provided. Another mechanism for assuring complete depression allows a mechanical signal to be transferred up the tube from the cutting device to indicate completion of the severing operation. This signal may be a compression-transmissive elongated member in a separate lumen of the tube wall, mechanically activated by the cutting member portion at full travel. Further, as noted above, the guide wire 3 may be provided with mild retraction, so that when the tissue is severed, it is urged into the tube. The release of the tension on the guide wire may also be used as a functional indicator of the completion of the severing operation.

At the tip of the biopsy device, a boring edge 53 is provided as the principal system for obtaining the tissue core. A central lobe 54 tapering to both sides of this sharpened steel member 71 allows a clean tissue cutting by the pressure of insertion, with a slight twisting or rotation. The lobe 54, along with the twisting, allows an inclined movement of the cutting edge with respect to the tissue to be cut, a preferred cutting method. Further, the cutting edge 50 faces forward during insertion of the device. Therefore, the sharpened cutting edge 50 may also assist in cutting the tissue core, although this is not its primary function, and it is preferred that the tissue be cylindrically cut before the cutting edge 50 reaches the tissue by a twisting of the biopsy instrument through an arc of ±90° about the long axis of the elongated tubular member 31 during insertion. In fact, an automated mechanism may also be provided to provide this twisting.

EXAMPLE 3

A multilobular boring edge may also be provided to reduce the amount of twisting necessary for this boring operation. The cutting edges 25, 26, in this case, are also provided with lobes 21, 22, and is involved in the boring operation as well. The lobes 21, 22 on the cutting edges 25, 26 may be helpful in severing the tissue core, acting in the same manner as the lobe 54 of the boring edge 53 to produce an effective inclination of the movement of the cutting edges 25, 26 with respect to the tissue to be cut. Because the cutting edges 25, 26 are involved in the boring operation, the edges 25, 26 are symmetric. Therefore, due to their symmetry, both edges 25, 26 move forward about a swing arc in the severing operation, in a jaw-like fashion to sever the tissue, reducing the cutting edge excursion approximately in half. Sliding steel members 32, 33 are provided linked to the sliding sleeve 36 by clamps 84, 87. The cutting edges 25, 26 are hinged about a flexion hinge 27, at a V-shaped notch 19, with a thin bridging portion 20. Opposite the V-shaped notch 19 is a V-shaped notch 18, which has separate edges linked to the counterbored groove 28, to form a hinge. These edges may be welded together. The trigger 40 simultaneously actuates both sliding steel members 29, 30, which may reduce trigger travel for full activation as compared to a single moving cutting member.

EXAMPLE 4

In construction, the cutting edge, boring edge, sliding member, hinge portions and means for attachment to the biopsy device of Example 1 and Example 3 are similar, shown in FIGS. 13–16 and 9–12 respectively, and formed of a single piece of stamped steel sheet. This steel sheet 70, 71 is divided into two lateral portions, the cutting side 26, 51 and the boring side 25, 53, linked by a narrow hinge section having a "V" notch 19, 57. The cutting edge 50, 24 has the steel sliding member 29 extending from a central portion thereof. The lateralmost edges of the cutting 18", 52" and boring 18', 52' portions are provided with means which cooperate to form a second hinge section, when rolled into a cylindrical form.

The side of the boring portion opposite the sharpened edge of the single-lobed embodiment of FIGS. 3, 13–16 is crimped 56 so that it can be inserted and firmly retained into a circular groove 60 in the end of the elongated tubular member 31. Thus, the sliding steel member 29 is inserted into the second aperture 80 of elongated tubular member, while boring portion 53 is mechanically attached in fixed relation to the elongated tubular member 31.

EXAMPLE 5

Figure 2:
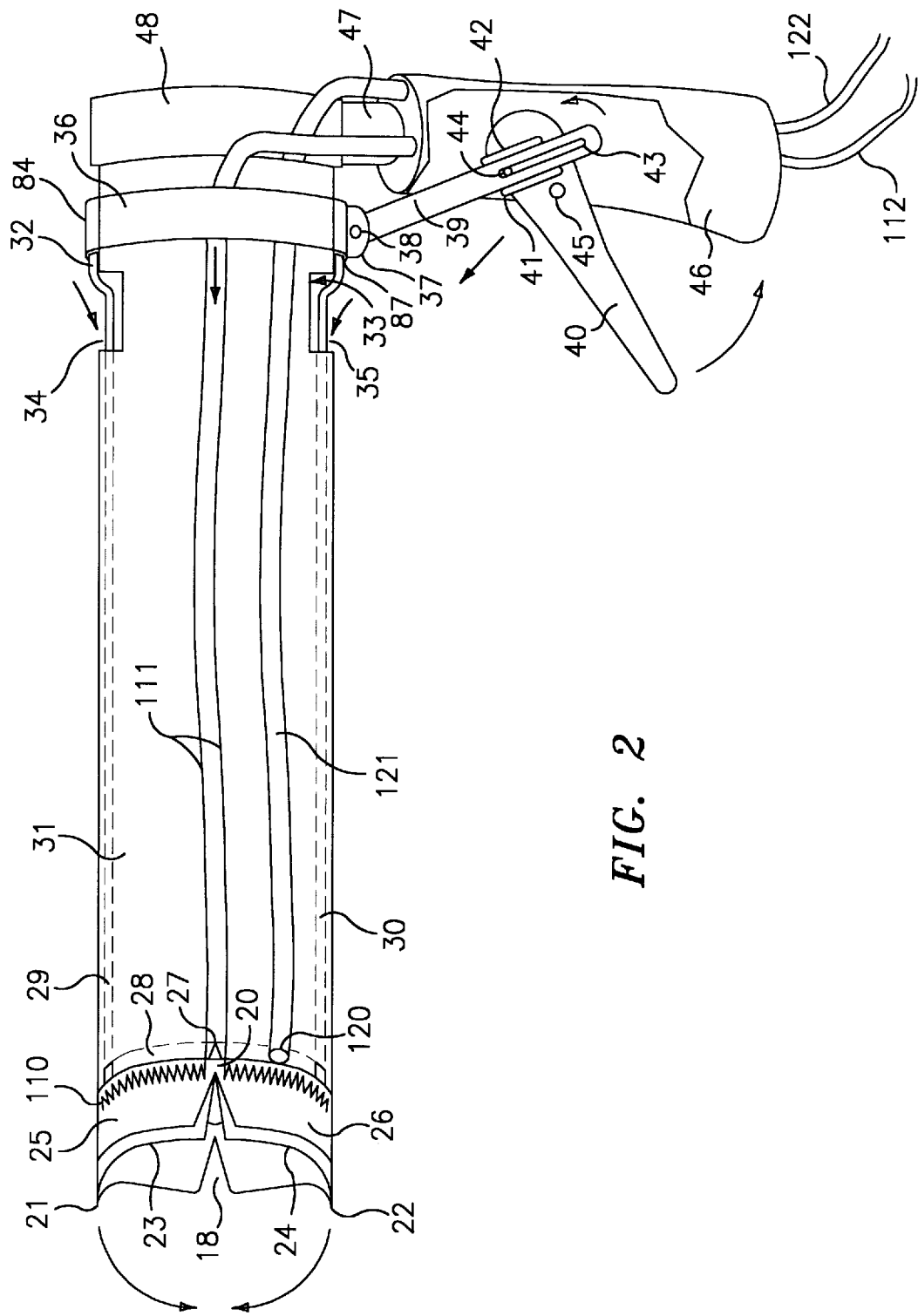
FIG. 2 shows a biopsy instrument according to a first embodiment of the present invention having two semicircular blades which move together to sever a tissue sample.

FIG. 2 also shows an optional electrosurgical device included with the instrument. In this case, an electrosurgical element 110, which is, for example, a heater as disclosed in U.S. Pat. No. 4,485,810 or an electrocautery system as disclosed in U.S. Pat No. 4,232,676, both of which are expressly incorporated herein by reference. The electrosurgical element is connected by wires 111, through a cable 112 from the handle 46 portion to an electrosurgical device control, not shown. A manually operated electrosurgical device control may be provided on the handle 46, or as a foot-pedal. In addition, the electrosurgical device may be automatically operated in conjunction with the trigger actuator 40.

EXAMPLE 6

Additionally, FIG. 2 shows an optical system for illuminating the area distal to the handle. For this purpose, a fiber optic member 121 is provided, having light emitting tip 120. The fiber optic member 121 is positioned inside, within the wall or outside of the elongated tubular member 31. The fiber optic member 121 is connected by fiber optic cable 122 to an external illumination source, not shown. In conjunction with an illumination system, an endoscopic viewing system and/or irrigation system may also be provided for use in conjunction with the instrument.

EXAMPLE 7

Figure 3:
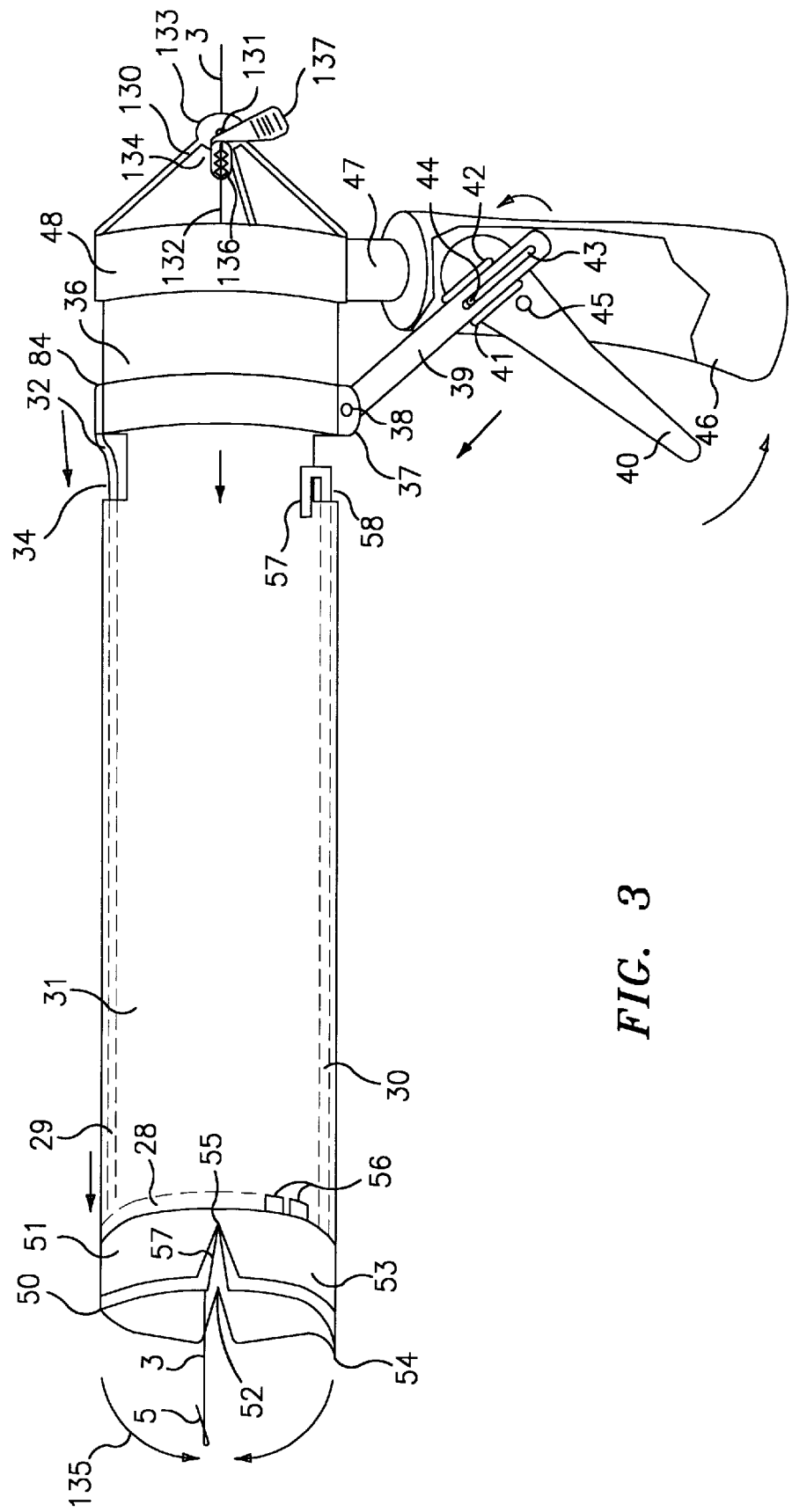
FIG. 3 shows a biopsy instrument according to a second embodiment of the present invention having a semicircular blade which moves toward a fixed blade to sever a tissue sample.
Figure 5:
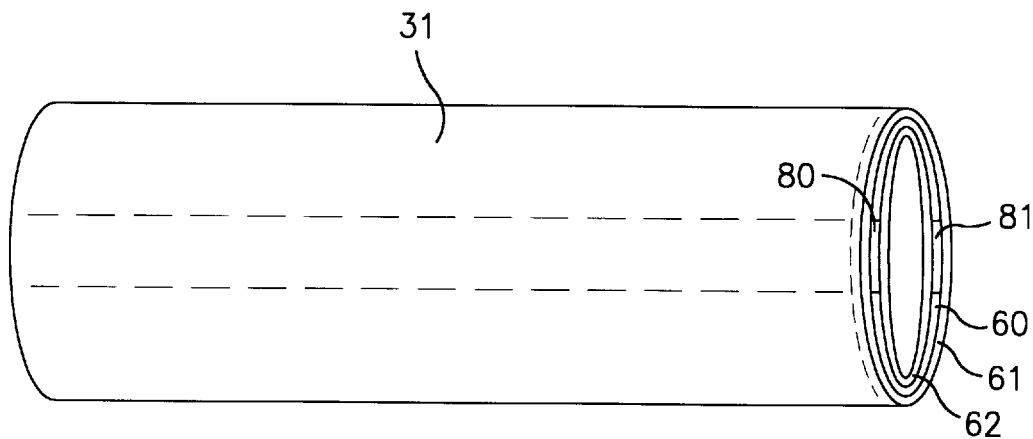
FIGS. 5, 6, 7 and 8 show a multilumen component of the biopsy instrument in a perspective, side, partial cross section and end views, respectively.
Figure 6:
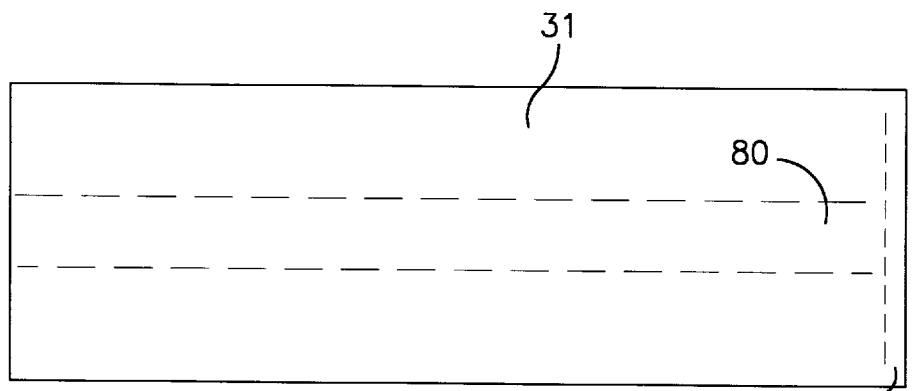
Figures 7, 8:
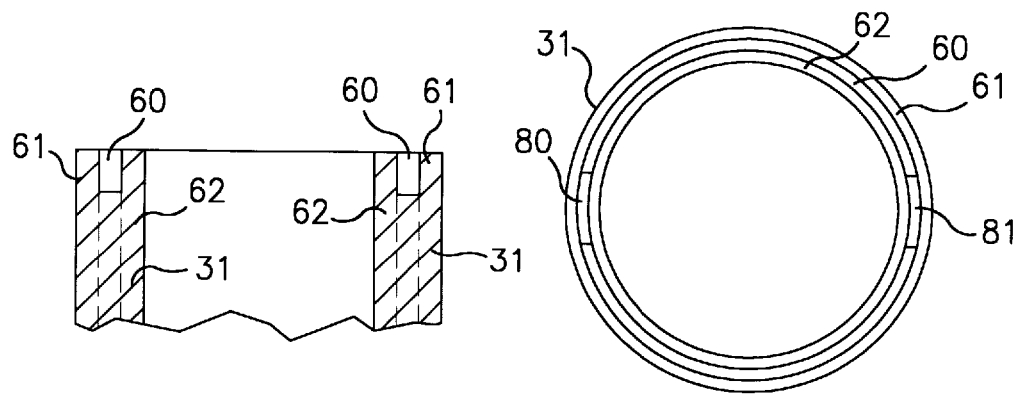
Figure 13:
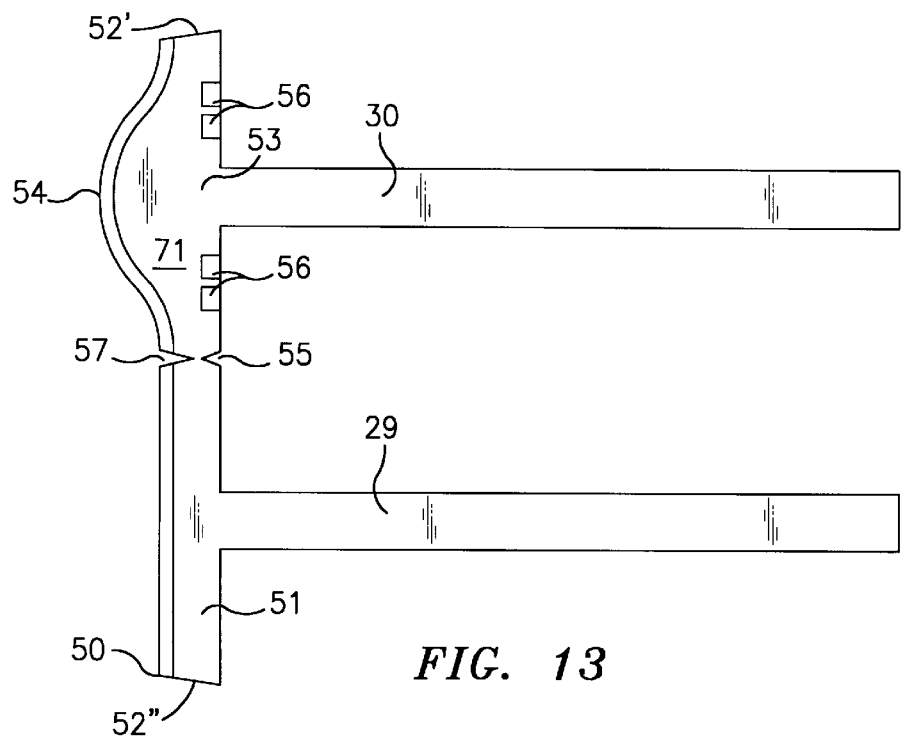
FIGS. 13, 14 and 15 show a blade member according to a second embodiment of the present invention having a lobed fixed blade, in top, side and folded views, respectively.
Figure 14:
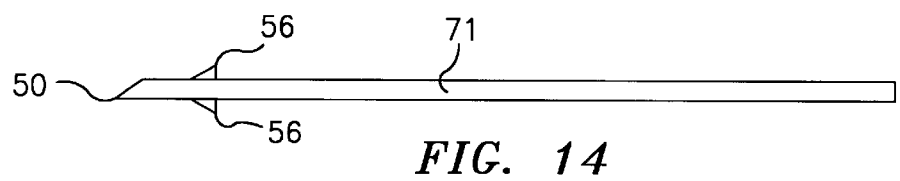
Figure 15:
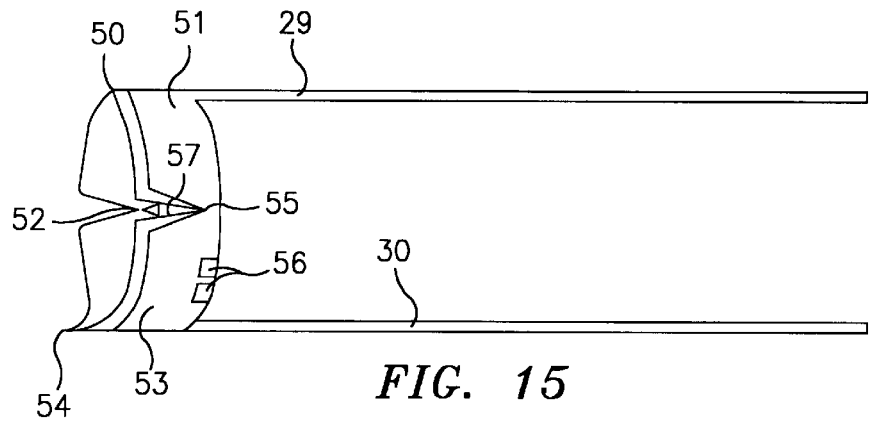
Figure 16:
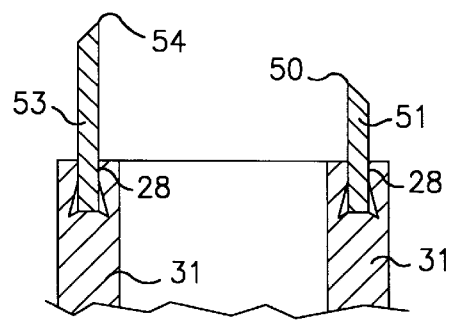
FIG. 16 shows the folded blade of FIG. 15, having expanded retaining portions on the lobed fixed blade.

FIG. 3 shows an optional guide wire retention mechanism. The guide wire 3, with barb 5, is inserted into suspect tissue 1, within the breast 2. The biopsy instrument is then positioned coaxially around the guide wire 3, with the guide wire 3 passing through an aperture 131 in a centering device 130. The guide wire 3 is provided with a length indicator position 132 at a fixed position from the barb 5. A "V" notch 133 may be provided to facilitate positioning of the guide wire 3 in the aperture 131. When the biopsy instrument is at an appropriate depth, as determined by a relative positioning of the length indicator position 132 with the aperture 131, a lock device 134, which mays also provide some compliance and apply a slight tension, clamps the guide wire 3 in fixed relation to the aperture 131. The lock device may include a set of serrated jaws 136 which clamp, by means of a manual clamping lever 137. Alternatively, a Jacob's-type chuck (not shown in the drawings) may be used to clamp the guide wire by twisting an outer locking ring, or another type locking mechanism may be employed. As the cutting edge 50 severs the breast tissue, the biopsy core sample will be within the lumen of the elongated tubular member 31 and retained in relative position during withdrawal of the biopsy instrument. This system also ensures that the suspect tissue is within a cutting arc 135 of the cutting edge 50.

EXAMPLE 8

A biopsy instrument is provided with a central guide cannula affixed to the device, the central guide cannula having a central aperture for following the guide wire to the suspected tumor. Because of the mass of the biopsy instrument, it may be preferable to have a detachable central guide cannula with is fed over the guide wire and then attached to the biopsy device. The guide wire then extends out from the rear of the instrument. The instrument is then guided among the path of the cannula and guide wire to the suspected tumor, penetrating the breast. The end of the cannula may be echogenic, allowing ultrasonic localization.

The biopsy instrument therefore includes one or more spider-type centering devices through which the stiffening cannula passes, which orient the biopsy device. Since the end of the stiffening cannula is preferably near the end of the guide wire or hook wire, the instrument must be displaceable with respect to the stiffening cannula along its axis. The stiffening cannula may also be locked in place with respect to the instrument, by means of, e.g., a compressed rubber frictional lock or a mechanical interlock. The lock is used to prevent the instrument from accidentally pushing into the breast tissue. A shroud may also be provided around the sharpened edges of the biopsy device, which is retracted when the instrument is immediately ready for use, exposing the sharp edges. The shroud increases the safety of the surgeon, hospital staff and patient. A marker is provided on the stiffening cannula or support system to indicate that the biopsy device has reached the desired location. The cutting tip of the biopsy device moves past the tips of the guide wire and the stiffening cannula and severs the biopsy specimen. The biopsy instrument is then withdrawn with the tissue sample, guide wire, and stiffening cannula inside. The tissue sample is then removed through the front of the instrument, preferably with the shroud in place, with the guide wire and stiffening cannula disengaged from the locking mechanism.

While the present invention is described with respect to specific illustrative embodiments thereof, which are not limiting on the scope of the invention, it will be understood that it is capable of further modifications and changes may be made without departing from the spirit and scope of the present invention. Therefore, the scope of the invention is limited only by the appended claims.

What is claimed is:

1. A surgical biopsy apparatus comprising:

a hollow elongated member, having an axis, and a distal end;

a circular sleeve member disposed radially around an exterior surface of the hollow elongated member;

a sharpened edge at a portion of said distal end for cutting tissue along said axis;

an actuator;

a sliding steel member connected to said actuator for extending towards the distal end upon actuation of the actuator;

an arm having first and second ends, said first end connected to said actuator and said second end connected to said circular sleeve member; and a cutting edge, linked to said actuator, by said sliding steel member, said cutting edge being moveable along a path including a transverse component to said axis, effective for severing tissue along said path.

2. The surgical biopsy apparatus according to claim 1, wherein said path is an arcuate path, said sharpened edge being pivoted about an axis near said distal end transverse to said axis of said hollow elongated member.

3. The surgical biopsy apparatus according to claim 1, further comprising means for localizing tissue to be biopsied.

4. The surgical biopsy apparatus according to claim 3, wherein said tissue localizing means is a guide wire.

5. The surgical biopsy apparatus according to claim 4, further comprising a guide wire centering device.

6. The surgical biopsy apparatus as claimed in claim 4 wherein said guide wire further includes a barbed retaining portion for extending into a tissue mass.

7. The surgical biopsy apparatus according to claim 3, wherein said tissue localizing means is a radiological apparatus.

8. The surgical biopsy apparatus according to claim 1, wherein said hollow elongated member is a tube having a round central lumen.

9. The surgical biopsy apparatus according to claim 1, wherein said hollow elongated member having at least two lumens, having a round central lumen and at least one eccentric lumen, each being smaller than said round central lumen.

10. The surgical biopsy apparatus according to claim 1, wherein said actuator causes a compression force to be transmitted to said cutting edge.

11. The surgical biopsy apparatus according to claim 9, wherein said actuator is mechanically linked to said cutting edge, to transmit said compression force.

12. The surgical biopsy apparatus according to claim 1, further comprising a tensile member for retracting a tissue core biopsy sample after being severed by said cutting edge.

13. The surgical biopsy apparatus according to claim 1, wherein said surgical biopsy apparatus is adapted for disposal after a single use.

14. The surgical biopsy apparatus according to claim 1, wherein said actuator communicates with said cutting edge by a method selected from the group consisting of mechanical tensile force, mechanical compressive force, mechanical torque, electric signal, pneumatic signal, and hydraulic signal.

15. The surgical biopsy apparatus according to claim 1, further comprising a guide wire locating member, and a system for ensuring that a tip of a guide wire located by said guide wire locating member is within a path of said cutting edge.

16. The surgical biopsy apparatus according to claim 1, wherein said cutting edge and said sharpened edge are formed from an integral sheet of metal.

17. The surgical biopsy apparatus according to claim 1, wherein said cutting edge is movable along said path by an extension integral with said cutting edge which travels within said hollow elongated member.

18. The surgical biopsy apparatus according to claim 17, wherein said integral extension is moved between a resting position and a severing position by a compressive force.

19. The surgical biopsy apparatus according to claim 1, further comprising an ergonomically adapted handle.

20. The surgical biopsy apparatus according to claim 19, wherein said actuator comprises a trigger affixed in proximity to said handle.

21. The surgical biopsy apparatus according to claim 1, wherein said sharpened edge includes a central lobe which tapers proximally on both sides.

22. The surgical biopsy apparatus according to claim 1, wherein said apparatus comprises radiotransparent materials.

23. The surgical biopsy apparatus according to claim 1, further comprising a unidirectional mechanism for actuating said cutting edge in a single direction.

24. A surgical biopsy apparatus comprising:

a hollow elongated member, having an axis, and a distal end;

a pair of sharpened edges at a portion of said distal end for cutting tissue along said axis;

an actuator; and a pivot axis near said distal end;

said actuator transmitting a signal to at least one of said sharpened edges, said signal causing said at least one sharpened edge to fold about said pivot axis toward said other sharpened edge, moving through an arcuate path, about said pivot axis, having a transverse component to said axis, effective for severing tissue along said path.

25. A surgical method, comprising:

identifying a tissue sample to be biopsied;

inserting a guide wire through the tissue sample;

inserting a biopsy instrument into a body, the instrument having:

a hollow elongated member, having an axis, and a distal end;

a sharpened edge at a portion of said distal end;

an actuator; and a pivot axis near said distal end, said actuator transmitting a signal to said sharpened edge causing said sharpened edge to fold about said pivot axis, to move through an arcuate path having a transverse component to said axis, effective for severing tissue along an said path;

forming a tissue core within the hollow elongated member;

actuating the actuator to cause the sharpened edge to fold, thereby severing a base of the tissue core from the body; and removing the instrument with the tissue core contained therewithin from the body.

* * * * *